(12) United States Patent
Yamada et al.

(10) Patent No.: US 10,107,793 B2
(45) Date of Patent: Oct. 23, 2018

(54) METHOD FOR RECOVERING METAL

(71) Applicant: ARKRAY, Inc., Kyoto (JP)

(72) Inventors: Hirofumi Yamada, Kyoto (JP); Akitsugu Kudo, Kyoto (JP)

(73) Assignee: ARKRAY, Inc., Kyoto (JP)

(*) Notice: Subject to any disclaimer, the term of this patent is extended or adjusted under 35 U.S.C. 154(b) by 0 days.

(21) Appl. No.: 14/632,145

(22) Filed: Feb. 26, 2015

(65) Prior Publication Data

US 2015/0247838 A1    Sep. 3, 2015

(30) Foreign Application Priority Data

Feb. 28, 2014 (JP) .................. 2014-039593
Feb. 26, 2015 (JP) .................. 2015-036116

(51) Int. Cl.
*G01N 33/493* (2006.01)
*G01N 1/34* (2006.01)
*G01N 33/84* (2006.01)

(52) U.S. Cl.
CPC ............. *G01N 33/493* (2013.01); *G01N 1/34* (2013.01); *G01N 33/84* (2013.01)

(58) Field of Classification Search
CPC .......... G01N 33/493; G01N 1/34; G01N 33/84
See application file for complete search history.

(56) References Cited

U.S. PATENT DOCUMENTS

| 5,126,272 A | 6/1992 | Kingston, Jr. et al. |
| 5,766,478 A | 6/1998 | Smith et al. |
| 8,232,105 B1 | 7/2012 | Scott |
| 2008/0318248 A1 | 12/2008 | Thorp, Jr. et al. |
| 2013/0017613 A1 | 1/2013 | Kaminski et al. |

FOREIGN PATENT DOCUMENTS

| CN | 102735524 A | 10/2012 |
| EP | 0509158 A1 | 10/1992 |
| EP | 2261656 A1 | 12/2010 |
| EP | 2508863 A2 | 10/2012 |
| EP | 2508864 A2 | 10/2012 |
| EP | 2572806 A1 | 3/2013 |
| JP | S61-50065 A | 3/1986 |
| JP | S61-209914 A | 9/1986 |
| JP | 2969226 B2 | 11/1999 |
| JP | 2013-079940 A | 5/2013 |
| WO | 01/34856 A1 | 5/2001 |

OTHER PUBLICATIONS

Extended European Search Report issued in corresponding European Patent Application No. 15157139.5 dated Jun. 2, 2015.

(Continued)

*Primary Examiner* — Samuel P Siefke

(74) *Attorney, Agent, or Firm* — Morgan, Lewis & Bockius LLP

(57) ABSTRACT

A method for recovering a metal that uses a reduced amount of a chelating agent is described, where the method includes a complex forming step of forming, in a mixture, a complex between a metal in a sample and a chelating agent; a complex depositing step of depositing the complex in the mixture; and a metal recovering step of recovering the deposited complex from the mixture, thereby recovering the metal in the sample.

17 Claims, 1 Drawing Sheet

(56) References Cited

OTHER PUBLICATIONS

"Mercury Analysis Manual," Ministry of the Environment, Japan (2004).
Office Action issued in related U.S. Appl. No. 14/632,217 dated Nov. 30, 2016.
Office Action issued in related U.S. Appl. No. 14/632,217 dated Feb. 3, 2017.
Office Action issued in corresponding European Patent Application No. 15157139.5 dated Feb. 8, 2017.
Moreno et al., "Simultaneous analysis of mercury and selenium species including chiral forms of selenomethionine in human urine and serum by HPLC column-switching coupled to ICP-MS," Analyst, 135: 2700-2705 (2010).
Shenashen et al., "Architecture of optical sensor for recognition of multiple toxic metal ions from water," Journal of Hazardous Materials, 260: 833-843 (2013).
Office Action issued in related European Patent Application No. 15157195.7 dated Oct. 16, 2017.
Office Action issued in related U.S. Appl. No. 14/632,217 dated Aug. 4, 2017.
Office Action issued in related U.S. Appl. No. 14/632,217 dated Jun. 29, 2016.
Office Action issued in related European Patent Application No. 15157195.7 dated Dec. 23, 2016.
Office Action issued in corresponding Japanese Patent Application No. 2015-036116 dated Mar. 6, 2018.
Office Action issued in corresponding Chinese Patent Application No. 201510091859.2 dated Feb. 9, 2018.
Extended European Search Report issued in related European Patent Application No. 18166697.5 dated May 15, 2018.

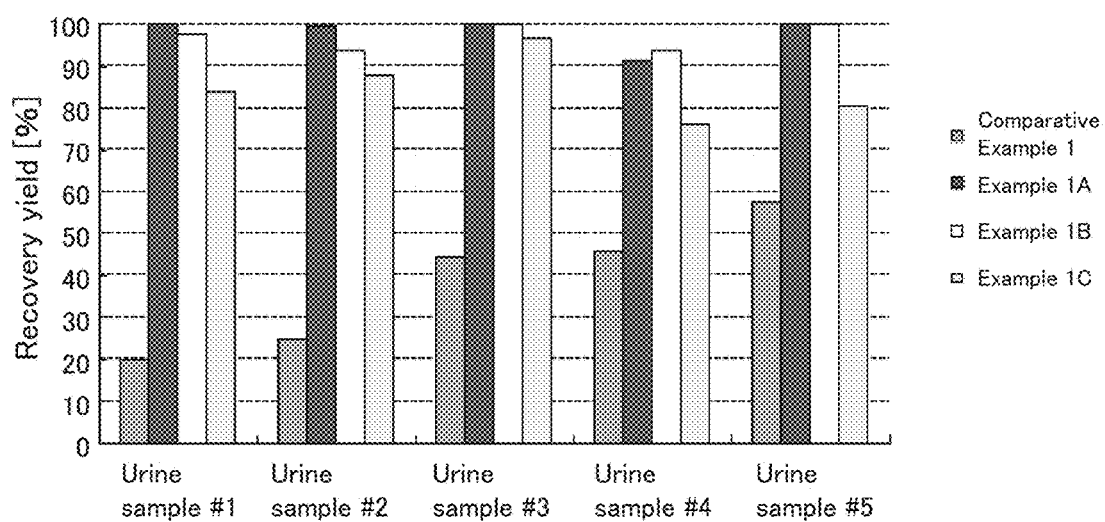

_US 10,107,793 B2_

METHOD FOR RECOVERING METAL

TECHNICAL FIELD

The present invention relates to a method for recovering a metal and a method for analyzing a metal.

BACKGROUND ART

It is known that metals such as mercury, cadmium, and lead are accumulated in human bodies, which results in adverse effects on health. Therefore, it is important to analyze metals in biological samples such as urine and the like and samples of food and beverages such as water and the like.

In the analysis of metals, generally, foreign substances are removed from a sample as a pretreatment to remove a metal(s), and the separated metal(s) is analyzed. As the pretreatment, a solvent extraction is widely used. The solvent extraction is a method in which a metal in a sample is extracted into an organic solvent by utilizing the polarity of a chelating agent to be bound to the metal according to the difference between the distribution coefficient of the metal in an aqueous solvent and in the organic solvent. The metal can be further concentrated by evaporating the organic solvent from the extracted fraction. As a specific example of the solvent extraction, a dithizone method using, as the chelating agent, 1,5-diphenyl-3-thiocarbazone (hereinafter, also referred to as "dithizone") that is insoluble in an aqueous solvent under acidic conditions is described in JIS, for example (see, Non Patent Literature 1 and Patent Literature 1). In the dithizone method, dithizone and a liquid sample are first mixed under acidic conditions to form a complex between the dithizone and a metal in the liquid sample in the mixture. Subsequently, an organic solvent such as carbon tetrachloride or chloroform is added to the mixture. Accordingly, the complex is extracted in the organic solvent because the distribution coefficient of the complex in the aqueous solvent is different from that of the complex in the organic solvent. By recovering this extracted fraction in the organic solvent, the metal can be recovered from the liquid sample as a complex. The metal can be further concentrated by further evaporating the organic solvent from the extracted fraction.

CITATION LIST

Patent Literature

Patent Literature 1: Japanese Patent No. 2969226

Non Patent Literature

Non Patent Literature 1: Mercury Analysis Manual, Ministry of the Environment, March 2004

SUMMARY OF INVENTION

Technical Problem

As described above, in the method for recovering a metal utilizing the formation of a complex between a chelating agent and the metal, the inventors of the present invention formulated a novel method for recovering the complex by filtering the mixture containing the complex without extracting the complex into an organic solvent.

However, there is a problem in that a metal cannot be recovered from a sample with superior efficiency without using a large amount of the chelating agent. In addition, since a large amount of the chelating agent is used, there is a problem in that the chelating agent is accumulated when the complex is recovered by filtration, which results in clogging.

Hence, the present invention is intended to provide a method for recovering a metal with a superior yield even when the amount of the chelating agent to be used is reduced.

In order to solve the above-described problems, the method for recovering a metal of the present invention includes; a complex forming step of forming, in a mixture, a complex between a metal in a sample and a chelating agent; a complex depositing step of depositing the complex in the mixture; and a metal recovering step of recovering the deposited complex from the mixture, thereby recovering the metal in the sample, where the method satisfies the following condition (1) or (2); the condition (1); the complex forming step and the complex depositing step are performed in parallel, wherein a sample with a pH adjusted to a pH in which the chelating agent is insoluble in an aqueous solvent and a chelate solution containing the chelating agent dissolved therein are mixed, thereby performing the formation and deposition of the complex in parallel; and the condition (2); the complex forming step and the complex depositing step are performed separately, wherein the complex forming step is a step of mixing the sample and the chelating agent to bring the metal in the sample and the chelating agent into a soluble state to be in contact with each other in the mixture, thereby forming a complex, and the complex depositing step is a step of adjusting the pH of the mixture to a pH in which the chelating agent is insoluble in an aqueous solvent after the complex forming step.

The method for analyzing a metal of the present invention includes: a metal recovering step of recovering a metal from a sample by the method of the present invention; and an analyzing step of analyzing the metal.

Although the mechanism is unknown, the complex can be formed efficiently according to the present invention even when the amount of the chelating agent to be used is reduced, for example. Accordingly, a metal can be recovered with a superior yield. Thus, the present invention is particularly useful in clinical examinations of samples derived from biological bodies and environmental testing, for example.

BRIEF DESCRIPTION OF DRAWING

FIG. 1 is a graph showing the complex recovery yield in Example 1.

DESCRIPTION OF EMBODIMENTS

<Method for Recovering a Metal>

As mentioned above, the method for recovering a metal of the present invention includes: a complex forming step of forming, in a mixture, a complex between a metal in a sample and a chelating agent; a complex depositing step of depositing the complex in the mixture; and a metal recovering step of recovering the deposited complex from the mixture, where the method satisfies the following condition (1) or (2): the condition (1): the complex forming step and the complex depositing step are performed in parallel, wherein a sample with a pH adjusted to a pH in which the chelating agent is insoluble in an aqueous solvent and a chelate solution containing the chelating agent dissolved therein are mixed, thereby performing the formation and deposition of the complex in parallel; and the condition (2): the complex forming step and the complex depositing step are performed separately, wherein the complex forming step is a step of mixing the sample and the chelating agent to bring the metal in the sample and the chelating agent into a soluble state to be in contact with each other in the mixture, thereby forming a complex, and the complex depositing step is a step of adjusting the pH of the mixture to a pH in which the chelating agent is insoluble in an aqueous solvent after the complex forming step.

The method for recovering a metal of the present invention (hereinafter referred to as "the metal recovery method of the present invention") is characterized in that a metal in a sample and a chelating agent in a soluble state are brought into contact with each other in a mixture in the complex forming step to form a complex between the metal and the chelating agent, and the other steps and conditions are not particularly limited.

According to the present invention, as mentioned above, a metal can be recovered with a superior yield. Thus, for example, variations in recovery yields among samples can be suppressed.

In the present invention, "a pH in which the chelating agent is soluble in an aqueous solvent" is referred to as "a soluble pH", and "a pH in which a chelating agent is insoluble in an aqueous solvent" is referred to as "an insoluble pH". There is a specific pH in which a chelating agent is soluble in an aqueous solvent depending on the kind of the chelating agent, and according to the common general technical knowledge at that time when the present application was filed, the pH in which a chelating agent is soluble in an aqueous solvent and the pH in which a chelating agent is insoluble in an aqueous solvent can be determined depending on the kind of chelating agent to be used.

In the metal recovery method of the present invention, a metal to be recovered is not particularly limited. Examples of the metal include heavy metals such as Bi (bismuth), Hg (mercury), Cd (cadmium), Pd (palladium), Zn (zinc), Tl (thallium), Ag (silver), and Pb (lead) and further include metals such as As (arsenic) and Al (aluminium). The form of the metal in the sample is not particularly limited and may be, for example, a single metal, an alloy of metals, or a metal-containing compound. The metal-containing compound may be, for example, a metal-containing organic compound or a metal-containing inorganic compound. In the case where the metal is Hg, Hg may be, for example, organic mercury or inorganic mercury. In the metal recovery method of the present invention, the metal to be recovered may be, for example, one kind or two or more kinds. In the metal recovery method of the present invention, two or more kinds of metals can be recovered from a sample in parallel by a single recovery process, for example.

The sample to which the metal recovery method of the present invention is applied is not particularly limited. Examples of the sample include a sample derived from a biological body, a sample derived from the environment, a chemical substance, and a pharmaceutical. Examples of the chemical substance include reagents, pesticides, and cosmetics. The sample derived from a biological body is not particularly limited, and examples thereof include urine, blood, hair, and umbilical cords. Examples of the blood sample include erythrocytes, whole blood, sera, and plasma. Among them, a urine sample is preferable. The sample derived from the environment is not particularly limited, and examples thereof include an organism, food, water, the ground, the atmosphere and air. The organism sample is not particularly limited, and examples thereof include animals such as fish and shellfish and plants. The food sample is not particularly limited, and examples thereof include fresh food and processed food. The water is not particularly limited, and examples thereof include drinking water, groundwater, river water, seawater, and domestic sewage.

A fluid sample (liquid sample) is preferable as the sample because it can be handled easily, for example. An undiluted liquid sample as it is or a diluted liquid sample obtained by suspending, dispersing, or dissolving the sample in a medium may be used as the liquid sample, for example. In the case where the sample is a solid, a diluted sample obtained by suspending, dispersing, or dissolving the sample in a medium may be used as the liquid sample, for example. Hereinafter, the medium is referred to as a "dilution medium". The dilution medium is not particularly limited, and examples thereof include water and a buffer solution. The buffer solution is not particularly limited, and examples thereof include a tris buffer solution, a phosphate buffer solution, an acetate buffer solution, a borate buffer solution, a citrate buffer solution, a veronal buffer solution, and various Good buffer solutions. The concentration of the buffer solution is not particularly limited and is, for example, from 10 to 100 mmol/L.

In the metal recovery method of the present invention, the chelating agent is not particularly limited. The chelating agent can be, for example, a chelating agent having a sulfur-containing group. The sulfur-containing group is a functional group having a sulfur atom. The sulfur-containing group is, for example, preferably a thioketone group. The thioketone group is not particularly limited, and examples thereof include a thiocarbazone group, a thiosemicarbazone group, a thiocarbadiazone group, a thiourea group, a thiosemicarbazide group, and a rubeamate group. In the metal recovery method of the present invention, the chelating agents may be used alone or in a combination of two or more, for example.

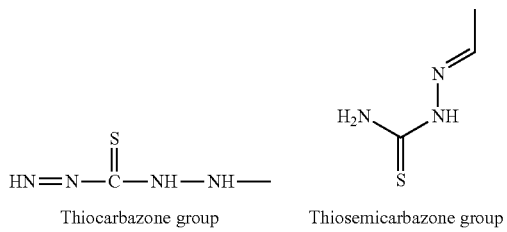

Thiocarbazone group    Thiosemicarbazone group

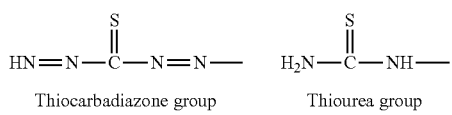

Thiocarbadiazone group    Thiourea group

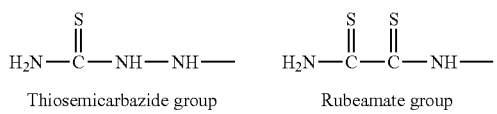

Thiosemicarbazide group    Rubeamate group

The chelating agent is, for example, preferably, a chelating agent represented by the following structural formula (4).

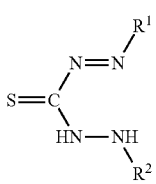
(4)

In the structural formula (4), $R^1$ and $R^2$ each represents a phenyl group. That is, the chelating agent represented by the structural formula (4) is a chelating agent having a thiocarbazone group and can be 1,5-diphenyl-3-thiocarbazone (dithizone). The structural formula (4) may represent a salt, for example.

Any hydrogen in the phenyl group may be substituted, for example. For example, the hydrogens in the phenyl group may be substituted by halogen or an alkali metal such as sodium or potassium when substituted.

Specific examples of the chelating agent having a sulfur-containing group include the following chelating agents. In the present invention, the following chelating agents are mere examples, and the present invention is not limited thereby.

(a1) Chelating agent having a thiocarbazone group e.g., 1,5-di(2-naphthyl)thiocarbazone;
(a2) Chelating agent having a thiosemicarbazone group e.g., acetone thiosemicarbazone, acetophenone thiosemicarbazone;
(a3) Chelating agent having a thiocarbadiazone group e.g., diphenylthiocarbadiazone;
(a4) Chelating agent having a thiourea group e.g., 1-acetyl-2-thiourea, guanyl thiourea, 1,3-bis(dimethylaminopropyl)-2-thiourea, tetramethyl thiourea, N,N'-diethyl thiourea, N,N'-diisopropyl thiourea, N,N'-dibutyl thiourea, 1,3-bis(dimethylaminopropyl)-2-thiourea, N-allyl-N'-(2-hydroxyethyl)thiourea, N,N'-bis(2-hydroxyethyl)thiourea, diacetyl thiourea, phenyl thiourea, N,N'-diphenyl thiourea, mono-o-tolyl thiourea, N,N'-di-o-tolyl thiourea, benzoyl thiourea;
(a5) Chelating agent having a thiosemicarbazide group e.g., phenylthiosemicarbazide, 4-phenylthiosemicarbazide, 4-methylthiosemicarbazide, thiosemicarbazide;
(a6) Chelating agent having a rubeamate group e.g., dithiooxamide (rubeanic acid).

In addition to the above-described chelating agents, examples of the chelating agents also include EDTA, NTA, DTPA, GLDA, HEDTA, GEDTA, TTHA, HIDA, and DHEG.

Examples of a soluble pH in which the chelating agent is soluble in an aqueous solvent and an insoluble pH in which the chelating agent is insoluble in an aqueous solvent are shown below. As mentioned above, in the present invention, the soluble pH and the insoluble pH can be determined depending on the kind of the chelating agent. Thus, the present invention is not limited by the examples.

A soluble pH is, for example, under alkaline conditions, where the lower limit of the soluble pH is more than pH 8, preferably pH 10 or more, and the upper limit of the soluble pH is not particularly limited and is, for example, pH 14 or less. In the case where the chelating agent is dithizone, the lower limit of the soluble pH is, for example, higher than pH 8, preferably pH 10 or more, and the upper limit of the soluble pH is not particularly limited and is, for example, pH 14 or less.

An insoluble pH is, for example, a pH lower than the soluble pH, and specific examples thereof include, pHs under acidic conditions (pH 5 or less), neutral conditions (pH 6 to 7), and alkaline conditions (higher than pH 7 to pH 8 or less). The upper limit of the insoluble pH is, for example, pH 8, preferably pH 6.8, more preferably pH 4, yet more preferably pH 3, particularly preferably pH 2. The lower limit of the insoluble pH is not particularly limited and is, for example, preferably pH 1. In the case where the chelating agent is dithizone, the upper limit of the insoluble pH is, for example, pH 8 or less, preferably pH 6.8 or less, and the lower limit of the insoluble pH is not particularly limited and is, for example, pH 1 or more.

In the complex forming step of the metal recovery method of the present invention, for example, the mixture may further contain a masking agent. In the present invention, "masking" means inactivating the reactivity of a SH group and can be performed by a chemical modification of a SH group, for example. The masking agent is not particularly limited, and for example, a known masking agent can be used and includes a SH inhibitor. The chemical modification is not particularly limited, and examples thereof include alkylation, addition to an active double bond, allylation, an exchange reaction with disulfide, oxidation, cyanidation, and mercaptidation.

As the masking agent, a compound represented by at least one structural formula selected from the group consisting of the following structural formulae (1) to (3) can be used, for example. The compounds represented by the following chemical formulae (1) to (3) may be used alone or in a combination of two or more, for example.

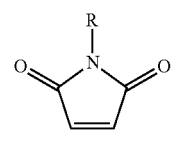
(1)

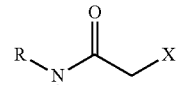
(2)

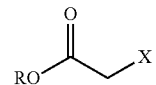
(3)

In the structural formula (1), R represents, for example, hydrogen, an alkyl group, a phenyl group, or a benzyl group. In the structural formula (2), R represents, for example, hydrogen, an alkyl group, a phenyl group, or a benzyl group, and X represents halogen. In the structural formula (3), R represents, for example, hydrogen, an alkyl group, a phenyl group, or a benzyl group, and X represents halogen.

The alkyl group is not particularly limited, and examples thereof include straight-chain or branched alkyl groups and aromatic alkyl groups. The carbon number of the alkyl group is, for example, from 1 to 7, preferably from 1 to 6, more preferably from 1 to 2, yet more preferably 2. Examples of the straight-chain or branched alkyl groups include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a n-hexyl group, an isohexyl group, a n-heptyl group, a n-octyl group, a n-nonyl group, and a n-decyl group. Any hydrogen in the alkyl group may be substituted or unsubstituted, for example.

Any hydrogen in the phenyl group and the benzyl group may be substituted or unsubstituted, for example. Examples of the halogen include fluorine, chlorine, bromine, and iodine.

Examples of the masking agent represented by the structural formula (1) include maleimide, N-methyl maleimide, N-ethyl maleimide, N-phenyl maleimide, and maleimide-propionic acid, and the masking agent is preferably N-ethyl maleimide. The compounds represented by the structural formula (1) may be used alone or in a combination of two or more.

The masking agent represented by the structural formula (2) can be, for example, halogenacetamide such as iodoacetamide and is preferably iodoacetamide. The compounds represented by the structural formula (2) may be used alone or in a combination of two or more.

The masking agent represented by the structural formula (3) can be, for example, a halogen acetic acid such as iodoacetic acid and is preferably iodoacetic acid. The compounds represented by the structural formula (3) may be used alone or in a combination of two or more.

In the metal recovery method of the present invention, the metal recovering step is, as mentioned above, a step of recovering a metal in a sample. In the present invention, for example, the complex recovered in the metal recovering step may be regarded as the metal, or the metal is isolated from the recovered complex by removing the chelating agent. In the latter case, in the present invention, the metal recovering step may further include a metal isolating step of isolating the metal from the recovered complex in addition to the complex recovering step of recovering the deposited complex.

Although the complex forming step and the complex depositing step are not particularly limited in the present invention, examples thereof include Embodiment 1 satisfying the condition (1) and Embodiment 2 satisfying the condition (2). Embodiments 1 and 2 are described below with reference to examples. Embodiment 1 can be described with reference to the description of Embodiment 2, and Embodiment 2 can be described with reference to the description of Embodiment 1, unless otherwise shown.

(1) Embodiment 1

Embodiment 1 is an embodiment satisfying the condition (1). That is, in Embodiment 1, the complex forming step and the complex depositing step are performed in parallel. Specifically, Embodiment 1 is an embodiment in which a sample with a pH adjusted to a pH in which the chelating agent is insoluble in an aqueous solvent and a chelate solution containing the chelating agent dissolved therein are mixed, thereby performing the formation and deposition of the complex in parallel. In Embodiment 1, the complex forming step and the complex depositing step are performed in parallel, and thus, these steps are hereinafter collectively referred to as a "complex forming and depositing step".

In Embodiment 1, a sample with a pH adjusted to the insoluble pH in advance and the chelate solution are mixed, thereby bringing the metal in the sample and chelating agent into contact with each other. Accordingly, a complex between the metal in the sample and the chelating agent can be formed and deposited in parallel.

For example, Embodiment 1 includes the following step (1a) as the complex forming and depositing step and the following step (1b) as the metal recovering step and optionally includes the following steps (1c) and (1d).

(1a) a step of mixing a sample with a pH adjusted to a pH in which the chelating agent is insoluble in an aqueous solvent and a chelate solution containing the chelating agent dissolved therein, thereby performing the formation and deposition of the complex in parallel (complex forming and depositing step);

(1b) a complex recovering step of recovering the deposited complex from the mixture, thereby recovering the complex;

(1c) a complex dissolving step of dissolving the recovered complex in an aqueous solvent;

(1d) a metal isolating step of isolating the metal from the complex.

In the complex forming and depositing step (1a) in Embodiment 1, a sample with a pH adjusted to the insoluble pH (hereinafter also referred to as a "pH-adjusted sample") is used. It is preferred that when the pH-adjusted sample and the chelate solution are mixed, the pH of the entire mixture becomes the insoluble pH by the insoluble pH of the sample according to the mixing process.

The insoluble pH can be determined appropriately according to the kind of the chelating agent to be used in the complex forming and depositing step (1a). As the insoluble pH, any of the above-mentioned examples can be employed, for example. In the case where the pH of a collected sample is originally the insoluble pH, the sample as it is may be mixed with the chelate solution. In the case where the pH of a collected sample is not the insoluble pH (e.g., the soluble pH), it is preferred that the pH is adjusted to the insoluble pH in advance, and the sample is then mixed with the chelate solution.

A method for adjusting the pH of the sample to the insoluble pH is not particularly limited, and for example, pH adjusting reagents such as an alkaline reagent, an acidic reagent, and a neutral reagent can be used.

Examples of the alkaline reagent include an alkali, an aqueous alkali solution, and a buffer solution under alkaline conditions. The alkali is not particularly limited, and examples thereof include sodium hydroxide and potassium hydroxide. Examples of the aqueous alkali solution include solutions obtained by diluting an alkali with water or a buffer solution. The buffer solution for use in the dilution of alkali is not particularly limited, and any of the above-mentioned common buffer solutions can be used. The concentration of alkali in the aqueous alkali solution is not particularly limited and is, for example, from 0.1N to 1N or more than 0N to $7 \times 10^{-3}$N or less. The buffer solution under alkaline conditions is not particularly limited, and examples thereof include Tris-NaOH, Tris-HCl, a carbonate buffer, and Good's buffers. The concentration of the buffer solution is not particularly limited and is, for example, from 10 to 100 mmol/L.

Examples of the acidic reagent include an acid, an aqueous acid solution, and a buffer solution under acidic conditions. The acid is not particularly limited, and examples thereof include hydrochloric acid, sulfuric acid, acetic acid, boric acid, phosphoric acid, and citric acid. Examples of the aqueous acid solution include solutions obtained by diluting an acid with water or a buffer solution. The buffer solution for use in the dilution of the acid is not particularly limited, and any of the above-mentioned common buffer solutions can be used. The concentration of acid in the aqueous acid solution is not particularly limited and is, for example, more than 0N to 5N or less, preferably from 0.01N to 5N, more preferably from 0.01N to 0.1N. The buffer solution under acidic conditions is not particularly limited, and examples thereof include a citrate buffer solution, an acetate buffer solution, a phosphate buffer solution, and Good's buffers. The concentration of the buffer solution is not particularly limited and is, for example from 10 to 100 mmol/L.

Examples of the neutral reagent include water, an aqueous neutral solution such as a saline solution, and a buffer solution under neutral conditions. The buffer solution under neutral conditions is not particularly limited, and examples thereof include a phosphate buffer solution and a tris buffer solution. The concentration of the buffer solution is not particularly limited and is, for example, from 10 to 100 mmol/L.

Examples of the chelate solution include a chelate solution obtained by dissolving the chelating agent in an aqueous solvent (hereinafter referred to as an "aqueous chelate solution") and a chelate solution obtained by dissolving the chelating agent in an amphipathic organic solvent (hereinafter referred to as an "organic chelate solution").

A method for preparing the aqueous chelate solution is not particularly limited, and for example, the aqueous chelate solution can be prepared by mixing the chelating agent and the aqueous solvent under the soluble pH conditions. Specific methods for preparing the aqueous chelate solution are not particularly limited, and for example, the aqueous chelate solution may be prepared by mixing an aqueous solvent with a pH adjusted to a soluble pH in advance and the chelating agent or by mixing the chelating agent and a pH-unadjusted aqueous solvent and thereafter adjusting the pH of the resultant mixture to a soluble pH.

The aqueous solvent is not particularly limited, and examples thereof include water and a buffer solution. The buffer solution is not particularly limited, and examples thereof include a tris buffer solution, a phosphate buffer solution, an acetate buffer solution, a borate buffer solution, a citrate buffer solution, a veronal buffer solution, and various Good buffer solutions. The concentration of the buffer solution is not particularly limited and is, for example, from 10 to 100 mmol/L.

The concentration of the chelating agent in the aqueous chelate solution is not particularly limited and is, for example, from 0.0001 to 0.1 g/mL, preferably from 0.0001 to 0.01 g/mL, more preferably from 0.0001 to 0.001 g/mL.

A method for preparing the organic chelate solution is not particularly limited, and for example, the organic chelate solution can be prepared by mixing the chelating agent and the amphipathic organic solvent.

The amphipathic organic solvent is not particularly limited as long as it is a hydrophilic organic solvent that can dissolve a chelating agent. The amphipathic organic solvent is not particularly limited, and examples thereof include acetone, methanol, ethanol, propanol, isopropanol, 1-butanol, 2-methyl-1-propanol, 2-butanol, 2-methyl-2-propanol, and DMSO.

The concentration of the chelating agent in the organic chelate solution is not particularly limited and is, for example, from 0.0001 to 0.1 g/mL, preferably from 0.0001 to 0.01 g/mL, more preferably from 0.0001 to 0.001 g/mL.

In the complex forming and depositing step (1a), the order of adding the sample and the chelate solution is not particularly limited. As a specific example, for example, the chelate solution may be added to the sample, or the sample may be added to the chelate solution.

A method for mixing the sample and the chelate solution is not particularly limited, and examples thereof include conventional methods such as mixing thoroughly, mixing by vibration, and mixing by ultrasound.

The mixing ratio (volume ratio (S:C)) between the sample (S) and the chelate solution (C) is not particularly limited and is, for example, S:C=1:0.0001 to 0.5, preferably S:C=1:0.0001 to 0.1, more preferably S:C=1:0.0001 to 0.01.

The composition ratio of the mixture is not particularly limited. The proportion (v/v %) of the sample in the mixture is not particularly limited and is, for example, 50% or more, preferably 80% or more, more preferably 90% or more. The proportion of an undiluted sample in the mixture is preferably in the above-described range.

The concentration of the chelating agent in the mixture is not particularly limited and is, for example, in the range from 0.0001 mg/mL or more to less than 0.1 mg/mL, preferably from 0.0001 mg/mL or more to 0.05 mg/mL or less, more preferably from 0.0001 mg/mL or more to 0.01 mg/mL or less. The concentration of the chelating agent may be, for example, a concentration of one kind of the chelating agent or a total of the concentrations of two or more kinds of the chelating agent.

In the mixture, the amount (by weight) of the chelating agent to be added relative to 1 mL of the sample is, for example, from 0.1 to 100 µg, preferably from 0.1 to 50 µg, more preferably from 0.1 to 10 µg.

In the complex forming and depositing step (1a), the mixture may further contain a masking agent, for example. In this case, the order of adding the masking agent is not particularly limited. As a specific example, for example, the masking agent may be mixed with a sample in advance, mixed with a chelate solution in advance, or added to the mixture. In the case where the chelate solution is an aqueous chelate solution containing a masking agent, it is preferred that the pH of the aqueous chelate solution containing a masking agent is set to a soluble pH, for example. The masking agent may be mixed before or after mixing a sample and a chelate solution or may be mixed in parallel with mixing a sample and a chelate solution, for example.

The concentration of the masking agent in the mixture is not particularly limited and is, for example, in the range from 5 to 30 mg/mL, preferably from 10 to 20 mg/mL. The concentration of the masking agent may be, for example, a concentration of the one kind of the masking agent or a total of the concentrations of two or more kinds of the masking agent.

The process conditions of the complex forming and depositing step (1a) are not particularly limited. The process temperature is, for example, room temperature. The lower limit of the process time is, for example, 30 seconds or more, the upper limit of the process time is, for example, 60 minutes or less, preferably 30 minutes or less, and the range of the process time is, for example, from 30 seconds to 60 minutes, preferably from 30 seconds to 30 minutes.

The complex recovering step (1b) is a step of recovering the deposited complex from the mixture. In the complex forming and depositing step (1a), the complex in the mixture is, as mentioned above, deposited in an insoluble state. Thus, in the complex recovering step (1b), the complex in an insoluble state, present in the mixture, is recovered.

A method for recovering the complex is not particularly limited, and for example, a known method for separating a solid and a liquid can be employed. Examples of the recovering method include processes such as filtration, centrifugal separation, precipitation, membrane separation, adsorption, and freeze-drying. The process conditions of the recovery are not particularly limited and can be set appropriately according to the kind and the amount of the complex, for example. For example, in the case where the complex is recovered by filtration, a filter to be used is not particularly limited, and examples thereof include a glass fiber filter paper, a filter paper, a filter paper powder, and a membrane filter. After the filtration, a fraction that does not pass through a filter can be recovered as the complex. For example, in the case where the complex is recovered by centrifugal separation, the conditions can include the centrifugal acceleration in the range from 19,600 to 29,400 m/s$^2$ (2,000 to 3,000×g), the temperature in the range from 4° C. to room temperature, and the time in the range from 1 to 10 minutes. For example, the complex can be recovered by removing a supernatant after the centrifugal separation.

In Embodiment 1, as mentioned above, the complex recovered in the complex recovering step may be regarded as the metal, a complex solution obtained by dissolving the complex in the optional complex dissolving step (1c) described below may be regarded as the metal, or the metal may be isolated by removing the chelating agent form the complex in the optional metal isolating step (1d) described below.

The complex dissolving step (1c) is a step of dissolving the recovered complex in an aqueous solvent. The chelating agent is dissolved in an aqueous solvent under a soluble pH as mentioned above. Therefore, the chelating agent in the complex state can be dissolved in an aqueous solvent by mixing the recovered complex and an aqueous solvent under soluble pH conditions. A solution obtained by dissolving the complex in an aqueous solvent is also referred to as an aqueous complex solution.

The aqueous solvent is not particularly limited, and any of the above-mentioned examples such as water and buffer solutions can be employed. As the soluble pH, any of the above-mentioned examples can be employed, for example. A method for adjusting the pH is not particularly limited, and the above-described pH adjusting reagents can be used. The pH may be adjusted utilizing the buffering capacity of the buffer solution, for example.

The order of mixing the complex and the aqueous solvent is not particularly limited, and for example, the aqueous solvent may be added to the complex, or the complex may be added to the aqueous solvent. The pH may be adjusted by adjusting the pH of the aqueous solvent to a soluble pH in advance or by adjusting the pH of the mixture obtained by mixing the complex and the aqueous solvent to a soluble pH, for example. In the former case, it is preferred that the pH of the entire mixture becomes the soluble pH by the soluble pH of the aqueous solvent according to the mixing process.

The amount of the aqueous solvent to be added relative to the complex is not particularly limited. The amount of the aqueous solvent to be added is, for example, preferably the amount in which the recovered complex can be dissolved. Moreover, the amount of the aqueous solvent to be added is, for example, preferably smaller than the liquid amount of the sample used in the complex forming and depositing step (1a). With this amount, for example, a metal-containing liquid with a concentration higher than the sample used can be obtained. That is, a metal-containing liquid in which a metal is concentrated compared with the sample can be obtained. The amount of the aqueous solvent to be added is, for example, in the range from ½ to ¹⁄₁₀₀, preferably from ¹⁄₁₀ to ¹⁄₅₀, more preferably ¹⁄₅₀, relative to the liquid amount of the sample.

For example, although it is preferred that the complex is completely dissolved in the aqueous solvent, the complex may partially remain in an insoluble state. The amount of the insoluble complex is, for example, preferably a detection limit or less.

A method for mixing the complex and the aqueous solvent is not particularly limited, and examples thereof include conventional methods such as mixing thoroughly, mixing by vibration, and mixing by ultrasound.

The metal isolating step (1d) is a step of isolating the metal from the complex. The complex recovered in the complex recovering step (1b) or the complex dissolved in the aqueous solvent in the complex dissolving step (1c) may be subjected to the metal isolating step (1d), for example.

In the metal isolating step (1d), the metal as a single metal can be recovered from the complex by decomposing the chelating agent in the complex, for example. A method for decomposing the chelating agent is not particularly limited and can be, for example, a known method such as ashing. Examples of the ashing include wet ashing and dry ashing. The wet ashing can be performed according to the Mercury Analysis Manual (Ministry of the Environment, March 2004), for example.

Embodiment 1 is described below with reference to an example where the soluble pH is under alkaline conditions, the insoluble pH is under acidic conditions, the chelating agent is dithizone, the dithizone solution is an aqueous dithizone solution obtained by dissolving dithizone in an aqueous alkaline solution, the sample is an urine sample, and the metal to be recovered is mercury. This, however, is merely an example and does not limit the present invention.

First, an urine sample is prepared. The amount of the urine sample is not particularly limited and is, for example, in the range from 1 to 100 mL, preferably from 1 to 20 mL, more preferably from 5 to 10 mL. The pH of the urine sample is then adjusted to be under acidic conditions by adding an acidic reagent. The pH of the pH-adjusted urine sample is, for example, from 1 to 8, preferably from 1 to 6.8.

Subsequently, an aqueous dithizone solution is prepared. The aqueous dithizone solution is prepared by adding an aqueous alkaline solution to freeze-dried dithizone. The pHs of the aqueous alkaline solution and the aqueous dithizone solution are, for example, from 9 to 12, preferably from 11 to 12. The concentration of dithizone in the aqueous dithizone solution is, for example, from 0.0001 to 0.1 mg/mL, preferably from 0.0001 to 0.01 mg/mL.

Then, the pH-adjusted urine sample and the aqueous dithizone solution are added to a tube to mix. The mixing ratio (volume ratio (S:C)) between the pH-adjusted urine sample (5) and the aqueous chelate solution (C) in the mixture is, for example, S:C=1:0.0001 to 0.5, preferably S:C=1:0.0001 to 0.1, more preferably S:C=1:0.0001 to 0.01. The amount of dithizone to be added relative to 1 mL of the urine sample is, for example, from 0.1 to 100 μg, preferably from 0.1 to 50 μg, more preferably from 0.1 to 10 μg. The pH of the mixture is, for example, an insoluble pH, preferably from 1 to 8, more preferably from 1 to 6.8.

The prepared mixture is left as is for a predetermined time to form and deposit a complex between dithizone and mercury in the urine sample in parallel. The process temperature is, for example, room temperature, the lower limit of the process time is, for example 30 seconds or more, the upper limit of the process time is, for example, 60 minutes or less, preferably 30 minutes or less, and the range of the process time is, for example, from 30 seconds to 60 minutes, preferably from 30 seconds to 30 minutes.

Subsequently, the mixture is filtrated with a filter, and a residue on the filter is recovered as the complex. The filter is, for example, as mentioned above.

A supernatant is removed, and an alkaline reagent is added to the residue on the filter. Accordingly, the complex is dissolved in the alkaline reagent.

The amount of the alkaline reagent to be added is not particularly limited and is, for example, in the range from 10 to 200 μL, preferably from 20 to 100 μL, more preferably 20 μL relative to 1 mL of the urine sample. The pH of the alkaline reagent is, for example, from 9 to 12, preferably from 11 to 12. The alkaline reagent is, for example, preferably an aqueous sodium hydroxide solution, and the normality thereof is, for example, in the range from 0.1N to 1N, preferably 0.4N. The pH of the mixture of the complex and the alkaline reagent is, for example, from 9 to 12, more preferably from 11 to 12.

Accordingly, mercury in the complex state, dissolved in the aqueous solvent, can be recovered. Moreover, for example, by subjecting the complex to wet ashing, the dithizone in the complex can be decomposed, and only mercury can be recovered. Although the recovery of mercury using an aqueous dithizone solution is described above as an example, the present invention is not limited thereto.

(2) Embodiment 2

Embodiment 2 is an embodiment satisfying the condition (2). That is, in Embodiment 2, the complex forming step and the complex depositing step are performed separately. Specifically, the complex forming step is a step of mixing a sample and a chelating agent to bring a metal in the sample and the chelating agent into a soluble state to be in contact with each other, thereby forming a complex. The complex depositing step is a step of adjusting the pH of the mixture to a pH in which the chelating agent is insoluble in an aqueous solvent after the complex forming step.

In Embodiment 2, a metal in the sample and the chelating agent in a soluble state are brought into contact with each other in the mixture. Accordingly, a complex between the metal in the sample and the chelating agent can be formed. The pH of the mixture is then adjusted to an insoluble pH to deposit the formed complex in the mixture.

For example, Embodiment 2 includes the following step (2a) as the complex forming step, the following step (2b) as the complex depositing step, and the following step (2c) as the metal recovering step and optionally includes the following steps (2d) and (2e).

(2a) a complex forming step of mixing a sample and a chelating agent to bring a metal in the sample and the chelating agent in a soluble state to be in contact with each other in the mixture, thereby forming a complex;
(2b) a complex depositing step of adjusting the pH of the mixture to a pH in which the chelating agent is insoluble in an aqueous solvent after the complex forming step, thereby depositing the complex in the mixture;
(2c) a complex recovering step of recovering the complex deposited from the mixture, thereby recovering the complex;
(2d) a complex dissolving step of dissolving the recovered complex in an aqueous solvent;
(2e) a metal isolating step of isolating the metal from the complex.

The steps (2c), (2d), and (2e) correspond to the steps (1b), (1c), and (1d) in Embodiment 1, respectively, and Embodiment 2 can be described with reference to the description of Embodiment 1.

Embodiment 2 can be Embodiment 2-1 using a chelate solution for mixing with a sample in the complex forming step (2a) or Embodiment 2-2 or 2-3 using a chelating agent in an insoluble state for mixing with a sample in the complex forming step (2a). Embodiments 2-1, 2-2, and 2-3 are described below with reference to the examples. Embodiments 2-1, 2-2, and 2-3 can be described with reference to any of the descriptions thereof, unless otherwise shown.

(2-1) Embodiment 2-1

For example, Embodiment 2-1 includes the following step (2a-1) using a chelate solution as the complex forming step (2a).

(2a-1) a complex forming step of mixing a sample and a chelate solution containing the chelating agent dissolved therein to bring a metal in the sample and the chelating agent into a soluble state to be in contact with each other in the mixture, thereby forming a complex;
(2b) a complex depositing step of adjusting the pH of the mixture to a pH in which the chelating agent is insoluble in an aqueous solvent after the complex forming step, thereby depositing the complex in the mixture;
(2c) a complex recovering step of recovering the complex deposited from the mixture, thereby recovering the complex;
(2d) a complex dissolving step of dissolving the recovered complex in an aqueous solvent;
(2e) a metal isolating step of isolating the metal from the complex The complex forming step (2a-1) is a step of mixing a sample and a chelate solution to bring a metal in the sample and the chelating agent into a soluble state to be in contact with each other in the mixture, thereby forming a complex. In the mixture, the chelating agent in a soluble state and the metal are brought to be in contact with each other, thereby forming the complex.

Examples of the chelate solution include an aqueous chelate solution obtained by dissolving a chelating agent in an aqueous solvent and an organic chelate solution obtained by dissolving a chelating agent in an amphipathic organic solvent. The aqueous chelate solution and the organic chelate solution can be described with reference to the description of Embodiment 1.

It is preferred that when the sample and the chelate solution are mixed in the complex forming step (2a-1), the pH of the entire mixture becomes the soluble pH by the pH (the soluble pH) of the chelate solution according to the mixing process. For example, although it is preferred that the chelating agent is maintained to be in the state of being completely dissolved in the mixture, the chelating agent may be in the state of being partially undissolved. In the latter case, for example, the chelating agent may be partially undissolved as long as the chelating agent in an amount in which a complex with a metal can be formed is present in the state of being dissolved in the mixture. The pH of the mixture may be adjusted to a soluble pH after the preparation of the mixture, for example.

In the complex forming step (2a-1), the pH of the sample is not particularly limited. It is preferred that the pH of the sample is, for example, the pH in which the pH of the mixture becomes a soluble pH when the sample and the chelate solution are mixed. For example, in the case where the sample is not an insoluble pH (e.g., a soluble pH), it is preferred that a pH-unadjusted sample is mixed as it is with a chelate solution. For example, in the case where the sample has an insoluble pH, the pH of the sample may be adjusted to a soluble pH in advance, and the sample and the chelate solution may be mixed. For example, in the case where the sample has an insoluble pH, it is preferred that the pH of the sample is adjusted to a pH in which the pH of the mixture becomes a soluble pH by the pH of the chelate solution. The pH can be adjusted using the above-described pH adjusting reagents, for example.

The order of mixing the sample and the chelate solution is not particularly limited, and for example, the chelate solution may be added to the sample, or the sample may be added to the chelate solution. A method for mixing the chelate solution and the sample is not particularly limited, and examples thereof include conventional methods such as mixing thoroughly, mixing by vibration, and mixing by ultrasound.

The mixing ratio (volume ratio (S:C)) between the sample (S) and the chelate solution (C) is not particularly limited and is, for example, S:C=1:0.0001 to 0.5, preferably S:C=1:0.0001 to 0.1, more preferably S:C=1:0.0001 to 0.01.

The composition ratio of the mixture is not particularly limited. The proportion (v/v %) of the sample in the mixture is not particularly limited and is, for example, 50% or more, preferably 80% or more, more preferably 90% or more. The proportion of an undiluted sample in the mixture is preferably in the above-described range.

The concentration of the chelating agent in the mixture is not particularly limited and is, for example, in the range from 0.0001 mg/mL or more to less than 0.1 mg/mL, preferably from 0.0001 mg/mL or more to 0.05 mg/mL or less, more preferably from 0.0001 mg/mL or more to 0.01 mg/mL or less. The concentration of the chelating agent may be a concentration of one kind of the chelating agent or a total of the concentrations of two or more kinds of the chelating agent.

In the mixture, the amount (by weight) of the chelating agent to be added relative to 1 mL of the sample is, for example, from 0.1 to 100 μg, preferably from 0.1 to 50 μg, more preferably from 0.1 to 10 μg.

In the complex forming step (2a-1), the mixture may further contain a masking agent and other components, for example. As the conditions of adding the masking agent and the other components, the conditions in Embodiment 1 can be employed, for example.

The process conditions in the complex forming step (2a-1) are not particularly limited, and the process temperature is, for example, room temperature, the lower limit of the process time is, for example, 30 seconds or more, the upper limit of the process time is, for example, 60 minutes or less, preferably 30 minutes or less, and the range of the process time is, for example, from 30 seconds to 60 minutes, preferably from 30 seconds to 30 minutes.

The complex depositing step (2b) is a step of adjusting the pH of the mixture to a pH in which the chelating agent is insoluble in an aqueous solvent after the complex forming step, thereby depositing the complex in the mixture. By adjusting the pH of the mixture to an insoluble pH, the chelating agent forming a complex with the metal becomes insoluble in the mixture. Thus, the complex between the insoluble chelating agent and the metal is deposited in an insoluble state in the mixture.

As the insoluble pH, any of the above-mentioned examples can be employed, for example. A method for adjusting the pH is not particularly limited, and the above-described pH adjusting reagents can be used as mentioned above.

The process conditions in the complex depositing step (2b) are not particularly limited, and the process temperature is, for example, room temperature, and the process time is, for example, from 30 seconds to 10 minutes.

For example, although it is preferred that the chelating agent is in the state of being completely undissolved in the mixture after adjusting the pH of the mixture to an insoluble pH, the chelating agent may be in the state of partially dissolved. In the latter case, for example, the chelating agent may be partially dissolved as long as the chelating agent forming the complex with the metal is present in an insoluble state in the mixture.

The steps (2c), (2d), and (2e) correspond to the steps (1b), (1c), and (1d) in Embodiment 1, respectively, and Embodiment 2-1 can be described with reference to the description of Embodiment 1.

Embodiment 2-1 is described below with reference to an example where the soluble pH is under alkaline conditions, the insoluble pH is under acidic conditions, the chelating agent is dithizone, the dithizone solution is an aqueous dithizone solution obtained by dissolving dithizone in an aqueous alkaline solution, the sample is an urine sample, and a metal to be recovered is mercury. This, however, is merely an example and does not limit the present invention.

First, an urine sample and an aqueous dithizone solution are prepared. The urine sample is preferably a pH-unadjusted sample.

Then, the urine sample and the aqueous dithizone solution are added to a tube to mix. The mixing ratio (volume ratio (S:C)) between the urine sample (S) and the aqueous chelate solution (C) in the mixture is, for example, S:C=1:0.0001 to 0.5, preferably S:C=1:0.0001 to 0.1, more preferably S:C=1:0.0001 to 0.01. The amount of dithizone to be added relative to 1 mL of the urine sample is, for example, from 0.1 to 100 μg, preferably from 0.1 to 50 μg, more preferably from 0.1 to 10 μg. The pH of the mixture may be a soluble pH and is, for example, from 9 to 12, preferably from 11 to 12.

The prepared mixture is left as is for a predetermined time to form a complex between dithizone in a soluble state and mercury in the urine sample. The process temperature is, for example, room temperature, the lower limit of the process time is, for example, 30 seconds or more, the upper limit of the process time is, for example, 60 minutes or less, preferably 30 minutes or less, and the range of the process time is, for example, from 30 seconds to 60 minutes, preferably from 30 seconds to 30 minutes.

Subsequently, the pH of the mixture is adjusted to be under acidic conditions by adding an acidic reagent. The adjusted pH of the prepared mixture is, for example, from 1 to 8, preferably from 1 to 6.8. The amount of the acidic reagent to be added is not particularly limited and can be set appropriately according to the kind of the acidic reagent.

The acidified mixture is left as it is for a predetermined time to deposit the complex between dithizone and mercury in the urine sample. The process temperature is, for example, room temperature, and the process time is, for example, from 30 seconds to 10 minutes.

The complex is then recovered and dissolved, and the metal is isolated therefrom in the same manner as in Embodiment 1.

(2-2) Embodiment 2-2

Embodiment 2-2 includes, as the complex forming step (2a), a complex forming step (2a-2) of, using a chelating agent in an insoluble state (hereinafter referred to as an "insoluble chelating agent"), adjusting the pH of the mixture to a soluble pH after mixing the insoluble chelating agent, for example.

(2a-2) a complex forming step of mixing a sample and a chelating agent in an insoluble state and adjusting the pH of the mixture to a pH in which the chelating agent is soluble in an aqueous solvent to cause the chelating agent in an insoluble state to be the chelating agent in a soluble state, thereby bringing the metal in the sample and the chelating agent into a soluble state to be in contact with each other and forming the complex;

(2b) a complex depositing step of adjusting the pH of the mixture to a pH in which the chelating agent is insoluble in an aqueous solvent after the complex forming step, thereby depositing the complex in the mixture;

(2c) a complex recovering step of recovering the complex deposited from the mixture, thereby recovering the complex;

(2d) a complex dissolving step of dissolving the recovered complex in an aqueous solvent;

(2e) a metal isolating step of isolating the metal from the complex

The complex forming step (2a-2) is a step of mixing a sample and an insoluble chelating agent and thereafter adjusting the pH of the mixture to a soluble pH to bring the metal in the sample and the chelating agent into a soluble state to be in contact with each other, thereby forming a complex. In the pH-adjusted mixture, the insoluble chelating agent is dissolved, and the chelating agent in a soluble state and the metal are brought to be in contact with each other, thereby forming the complex.

The insoluble chelating agent is not particularly limited and may be, for example, in the solid state (also referred to as the "dry state") or in the liquid state. In the latter case, the chelating agent is, for example, preferably a chelate dispersion liquid obtained by dispersing the chelating agent in an insoluble state in an aqueous solvent.

A method for preparing the chelate dispersion liquid is not particularly limited and can be, for example, prepared by mixing the chelating agent and the aqueous solvent under the insoluble pH, for example. A specific method is not particularly limited, and for example, the chelate dispersion liquid may be prepared by mixing an aqueous solvent with a pH adjusted to an insoluble pH in advance and the chelating agent or by mixing the chelating agent and a pH-unadjusted aqueous solvent and thereafter adjusting the pH of the mixture to an insoluble pH.

The concentration of the chelating agent in the chelate dispersion liquid is not particularly limited and is, for example, from 0.0001 to 0.1 g/mL, preferably from 0.0001 to 0.01 g/mL, more preferably from 0.0001 to 0.001 g/mL.

In the complex forming step (2a-2), when the sample and the insoluble chelating agent are mixed, the pH of the entire mixture is, for example, preferably, an insoluble pH.

In the complex forming step (2a-2), the pH of the sample is not particularly limited. It is preferred that Embodiment 2-2 is applied to the case where the pH of the sample is an insoluble pH, specifically the case where the pH of the mixture becomes an insoluble pH when the sample and the insoluble chelating agent are mixed.

The order of mixing the sample and the insoluble chelating agent is not particularly limited, and for example, the insoluble chelating agent may be added to the sample, or the sample may be added to the insoluble chelating agent. A method for mixing the insoluble chelating agent and the sample is not particularly limited, and examples thereof include conventional methods such as mixing thoroughly, mixing by vibration, and mixing by ultrasound.

In the case where the chelating agent is the chelate dispersion liquid, the mixing ratio (volume ratio (S:C)) between the sample (S) and the chelate dispersion liquid (C) is not particularly limited and is, for example, S:C=1:0.0001 to 0.5, preferably S:C=1:0.0001 to 0.1, more preferably S:C=1:0.0001 to 0.01.

The concentration of the chelating agent in the mixture is not particularly limited and is, for example, in the range from 0.0001 mg/mL or more to less than 0.1 mg/mL, preferably from 0.0001 mg/mL or more to 0.05 mg/mL or less, more preferably from 0.0001 mg/mL or more to 0.01 mg/mL or less. The concentration of the chelating agent may be, for example, a concentration of one kind of the chelating agent or a total of the concentrations of two or more kinds of the chelating agent.

In the mixture, the amount (by weight) of the chelating agent to be added relative to 1 mL of the sample is, for example, from 0.1 to 100 µg, preferably from 0.1 to 50 µg, more preferably from 0.1 to 10 µg.

In the complex forming step (2a-2), the pH of the mixture is adjusted to a soluble pH after mixing the sample and the insoluble chelating agent. By adjusting the pH of the mixture to a soluble pH, the state of the chelating agent is changed from an insoluble state to a soluble state, and in the mixture, the chelating agent in a soluble state and the sample are brought to be in contact with each other, and the complex is formed.

As the soluble pH, any of the above-mentioned examples can be employed, for example. A method for adjusting the pH is not particularly limited, and the above-described pH adjusting reagents can be used as mentioned above.

For example, although it is preferred that the chelating agent is in the state of being completely dissolved in the mixture by the adjustment to a soluble pH, the chelating agent may be in the state of being partially undissolved. In the latter case, for example, the chelating agent may be partially undissolved as long as the chelating agent in an amount in which a complex with a metal can be formed is present in the state of being dissolved in the pH-adjusted mixture.

The process conditions of the complex forming step (2a-2) are not particularly limited, and the process temperature is, for example, room temperature, the lower limit of the process time is, for example, 30 seconds or more, the upper limit of the process time is, for example, 60 minutes or less, preferably 30 minutes or less, the range of the process time is, for example, from 30 seconds to 60 minutes, preferably from 30 seconds to 30 minutes, and the process time after the adjustment to a soluble pH is preferably in the above-mentioned range.

In the complex forming step (2a-2), the mixture may further contain a masking agent and other components, for example. As the conditions of adding the masking agent and the other components, the conditions in Embodiment 1 can be employed, for example.

The step (2b) is the same as the step (2b) in Embodiment 2-1, and the steps (2c), (2d), and (2e) correspond to the steps (1b), (1c), and (1d) in Embodiment 1, respectively, and Embodiment 2-2 can be described with reference to the descriptions of Embodiments 1 and 2-1.

Embodiment 2-2 is described below with reference to an example where the soluble pH is under alkaline conditions, the insoluble pH is under acidic conditions, the chelating agent is insoluble dithizone in the solid state, the sample is an urine sample, and the metal to be recovered is mercury. This, however, is merely an example and does not limit the present invention.

First, an urine sample is prepared in the same manner as in Embodiment 2-1. Then, freeze-dried dithizone and the urine sample are added to a tube to mix. The amount of dithizone to be added relative to 1 mL of the urine sample is, for example, from 0.1 to 100 µg, preferably from 0.1 to 50 μg, more preferably from 0.1 to 10 μg. The pH of the mixture is, for example, from 1 to 8, preferably from 1 to 6.8.

Subsequently, the pH of the mixture is adjusted to be under alkaline conditions by adding an alkaline reagent. The adjusted pH of the mixture is, for example, preferably from 9 to 12, more preferably from 11 to 12. The amount of the alkaline reagent to be added is not particularly limited and is, for example, in the range from 10 to 200 μL, preferably from 20 to 100 μL, more preferably 20 μL relative to 1 mL of the urine sample. The pH of the alkaline reagent is, for example, from 9 to 12, preferably from 11 to 12. The alkaline regent is, for example, preferably an aqueous sodium hydroxide solution, and the normality thereof is, for example, in the range from 0.1N to 1N, preferably 0.4N.

The mixture adjusted to be under alkaline conditions is left as it is for a predetermined time to form a complex between dithizone and mercury in the urine sample. The process temperature is, for example, room temperature, the lower limit of the process time is, for example, 30 seconds or more, the upper limit of the process time is, for example, 60 minutes or less, preferably 30 minutes or less, and the range of the process time is, for example, from 30 seconds to 60 minutes, preferably from 30 seconds to 30 minutes.

Subsequently, the complex is deposited, recovered, and dissolved, and the metal is isolated in the same manner as in Embodiment 2-1.

(2-3) Embodiment 2-3

Embodiment 2-3 includes a complex forming step (2a-3) of, using a chelate solution, mixing the chelate solution in a sample with a pH adjusted to a soluble pH as the complex forming step (2a), for example.

(2a-3) a complex forming step of mixing a sample with a pH in which the chelating agent is soluble in an aqueous solvent and the chelating agent in an insoluble state to cause the chelating agent in an insoluble state to be the chelating agent in a soluble state, thereby bring a metal in the sample and the chelating agent into a soluble state to be in contact with each other in the mixture and forming a complex;
(2b) a complex depositing step of adjusting the pH of the mixture to a pH in which the chelating agent is insoluble in an aqueous solvent after the complex forming step, thereby depositing the complex in the mixture;
(2c) a complex recovering step of recovering the complex deposited from the mixture, thereby recovering the complex;
(2d) a complex dissolving step of dissolving the recovered complex in an aqueous solvent;
(2e) a metal isolating step of isolating the metal from the complex The complex forming step (2a-3) is a step of mixing a sample with a pH adjusted to a soluble pH in advance and the insoluble chelating agent to bring a metal in the sample and the chelating agent into a soluble state to be in contact with each other in the mixture, thereby forming a complex. In the mixture, the insoluble chelating agent is dissolved to bring the chelating agent into a soluble state and the metal to be in contact with each other, thereby forming the complex.

The insoluble chelating agent is not particularly limited and is, for example, the same as in Embodiment 2-2 and is, for example, preferably a chelate dispersion liquid.

As the soluble pH, any of the above-mentioned examples may be employed, for example. A method for adjusting the pH is not particularly limited, and the above-described pH adjusting reagents can be used as mentioned above.

In the complex forming step (2a-3), the pH-adjusted sample preferably has a pH in which the pH of the mixture becomes a soluble pH when the sample and the insoluble chelating agent are mixed, for example. In the case where the pH of a collected sample is originally a soluble pH, the sample as it is may be mixed with the insoluble chelating agent. In the case where the pH of a collected sample is not a soluble pH (e.g., an insoluble pH), it is preferred that the pH of the sample is adjusted to a soluble pH in advance, and the sample is then mixed with the insoluble chelating agent.

The order of mixing the sample and the chelating agent is not particularly limited, and for example, the chelating agent may be added to the sample, or the sample may be added to the chelating agent. A method for mixing the chelating agent and the sample is not particularly limited, and examples thereof include conventional methods such as mixing thoroughly, mixing by vibration, and mixing by ultrasound.

In the case where the chelating agent is the chelate dispersion liquid, the mixing ratio (volume ratio (S:C)) between the sample (S) and the chelate dispersion liquid (C) is not particularly limited and is, for example, S:C=1:0.0001 to 0.5, preferably S:C=1:0.0001 to 0.1, more preferably S:C=1:0.0001 to 0.01.

The concentration of the chelating agent in the mixture is not particularly limited and is, for example, in the range from 0.0001 mg/mL or more to less than 0.1 mg/mL, preferably from 0.0001 mg/mL or more to 0.05 mg/mL or less, more preferably from 0.0001 mg/mL or more to 0.01 mg/mL or less. The concentration of the chelating agent may be, for example, a concentration of one kind of the chelating agent or a total of the concentrations of two or more kinds of the chelating agent.

In the mixture, the amount (by weight) of the chelating agent to be added relative to 1 mL of the sample is, for example, from 0.1 to 100 μg, preferably from 0.1 to 50 μg, more preferably from 0.1 to 10 μg.

The process conditions in the complex forming step (2a-3) are not particularly limited, and the process temperature is, for example, room temperature, the lower limit of the process time is, for example, 30 seconds or more, the upper limit of the process time is, for example, 60 minutes or less, preferably 30 minutes or less, and the range of the process time is, for example, from 30 seconds to 60 minutes, preferably from 30 seconds to 30 minutes.

In the complex forming step (2a-3), the mixture may further contain a masking agent and other components, for example. As the conditions of adding the masking agent and the other components, the conditions in Embodiment 1 can be employed, for example.

The step (2b) is the same as the step (2b) in Embodiment 2-1, the steps (2c), (2d), and (2e) correspond to the steps (1b), (1e), and (1d) in Embodiment 1, respectively, and Embodiment 2-3 can be described with reference to the descriptions of Embodiments 1 and 2-1.

Embodiment 2-3 is described below with reference to an example where the soluble pH is under alkaline conditions, the insoluble pH is under acidic conditions, the chelating agent is insoluble dithizone in the solid state, the sample is an urine sample, and the metal to be recovered is mercury. This, however, is merely an example and does not limit the present invention.

First, an urine sample is prepared in the same manner as in Embodiment 2-1, and the pH of the urine sample is adjusted to be under alkaline conditions by adding an alkaline reagent. The adjusted pH of the urine sample is, for example, preferably from 9 to 12, more preferably from 11 to 12. The amount of the alkaline reagent to be added is not particularly limited and is, for example, in the range from 10 to 200 μL, preferably from 20 to 100 μL, more preferably 20 μL relative to 1 mL of the urine sample. The pH of the alkaline reagent is, for example, from 9 to 12, preferably from 11 to 12. The alkaline regent is, for example, preferably an aqueous sodium hydroxide solution, and the normality thereof is, for example, in the range from 0.1N to 1N, preferably 0.4N.

Then, freeze-dried dithizone and the pH-adjusted urine sample are added to a tube to mix. The amount of dithizone to be added relative to 1 mL of the urine sample is, for example, from 0.1 to 100 μg, preferably from 0.1 to 50 μg, more preferably from 0.1 to 10 μg. The pH of the mixture is, for example, from 9 to 12, preferably from 11 to 12.

The prepared mixture is left as is for a predetermined time to form a complex between dithizone and mercury in the urine sample. The process temperature is, for example, room temperature, and the process time is, for example, from 30 seconds to 10 minutes.

Subsequently, the complex is deposited, recovered, and dissolved, and the metal is isolated in the same manner as in Embodiment 2-1.

(3) Embodiment 3

The metal recovery method of the present invention may be, for example, Embodiment 3 further using a second chelating agent in Embodiments 1 and 2 using a chelating agent (hereinafter referred to as a "first chelating agent") in the complex forming step, for example.

Embodiment 3 is an embodiment in which a metal derived from a complex (hereinafter referred to as a "first complex") between a first chelating agent and the metal, recovered in the metal recovering step, is recovered in an aqueous solvent containing a second chelating agent that is different in kind from the first chelating agent. In this case, Embodiment 3 can be Embodiment 3-1 using a chelating agent represented by the structural formula (5) described below as the second chelating agent or Embodiment 3-2 using a chelating agent represented by the structural formula (6) described below as the second chelating agent. Embodiments 3-1 and 3-2 are described below.

(3-1) Embodiment 3-1

First, Embodiment 3-1 is, as mentioned above, an embodiment using a chelating agent represented by the following structural formula (5) as the second chelating agent and shows an example of recovering a first complex between a first chelating agent and a metal and recovering the metal derived from the first complex in an aqueous solvent containing the second chelating agent.

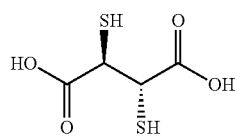

(5)

The second chelating agent represented by the structural formula (5) is meso-2,3-dimercapto succinic acid (DMSA). Hereinafter, the second chelating agent is also referred to as DMSA.

Embodiment 3-1 further includes the following steps (3a), (3b), and (3c) after the metal recovering step of recovering the complex (first complex).

(3a) a second complex forming step of preparing, under the pH conditions where a first chelating agent is insoluble in an aqueous solvent, and the second chelating agent is soluble in an aqueous solvent, a mixture of a recovered first complex and an aqueous second chelating agent solution obtained by dissolving the second chelating agent in an aqueous solvent, thereby forming a second complex between the metal derived from the first complex and the second chelating agent in the mixture (3b) a second complex recovering step of recovering a liquid fraction containing the second complex dissolved therein from the mixture (3c) a metal isolating step of isolating the metal from the second complex (3a) Second Complex Forming Step The second complex forming step is a step of preparing, under the pH conditions where a first chelating agent is insoluble in an aqueous solvent, and the second chelating agent is soluble in an aqueous solvent, a mixture of a recovered first complex and an aqueous second chelating agent solution obtained by dissolving the second chelating agent in an aqueous solvent (hereinafter referred to as an "aqueous second chelate solution"), thereby forming a second complex between the metal derived from the first complex and the second chelating agent in the mixture.

The "pH in which a second chelating agent is soluble in an aqueous solvent" is hereinafter referred to as a "second chelating agent soluble pH", and the "pH in which a second chelating agent is insoluble in an aqueous solvent" is hereinafter referred to as a "second chelating agent insoluble pH". The insoluble pH of the first chelating agent is referred to as a "first insoluble pH", and the pH in which the first chelating agent is insoluble in an aqueous solvent, and the second chelating agent is soluble in an aqueous solvent is referred to as a "second insoluble pH".

The second chelating agent soluble pH is, for example, preferably the second insoluble pH in which the first chelating agent is insoluble in an aqueous solvent. The second insoluble pH can be, for example, a pH under non-alkaline conditions, and specific examples thereof include pHs under acidic conditions (pH 2 to 3), mildly acidic conditions (pH 4 to 5), and neutral conditions (pH 6 to 7). The upper limit of the second insoluble pH is not particularly limited and is, for example, pH6.8, preferably pH6, more preferably pH4. The lower limit of the second insoluble pH is not particularly limited and is, for example, pH2, preferably pH3, more preferably pH4. The second insoluble pH can be set appropriately according to the kinds and the like of the first and second chelating agents, for example.

For example, although it is preferred that the second chelating agent is in the state of being completely dissolved, the second chelating agent may be in the state of being partially dissolved. In the latter case, for example, the second chelating agent may be partially dissolved as long as the second chelating agent in an amount in which a complex with the metal derived from the first complex can be formed is present in the aqueous solution, for example.

A method for preparing the aqueous second chelate solution is not particularly limited, and for example, the aqueous second chelate solution may be prepared by adjusting the pH of an aqueous solvent to a second insoluble pH and thereafter dissolving the second chelating agent or by adding the second chelating agent to an aqueous solvent and thereafter adjusting the pH of the mixture to a second insoluble pH to dissolve the second chelating agent.

In the former case, since DMSA as the second chelating agent is a strong acid, it is preferred that an aqueous solvent in which the second chelating agent is dissolved is, for example, an alkaline reagent. By dissolving the second chelating agent in an alkaline reagent, an aqueous solution with a second insoluble pH, preferably under non-alkaline conditions, can be prepared.

In the latter case, the aqueous solvent is not particularly limited, and for example, any of water, an aqueous solution, a buffer solution, and the like can be used. For example, the aqueous solvent and the second chelating agent may be mixed, and thereafter, the pH of the mixture may be adjusted to a second insoluble pH. A method for adjusting the pH is not particularly limited, and for example, the above-described pH adjusting reagents can be used appropriately.

The concentration of the second chelating agent in the aqueous second chelate solution is not particularly limited and is, for example, from 5 to 20 mg/mL, preferably from 10 to 20 mg/mL.

A method for mixing the first complex and the aqueous second chelate solution is not particularly limited, and examples thereof include conventional methods such as mixing thoroughly, mixing by vibration, and mixing by ultrasound.

In the mixture, the amount of the aqueous second chelate solution to be added is not particularly limited and is, for example, from 10 to 200 µL, preferably from 20 to 100 µL, more preferably 20 µL relative to 1 mL of the sample used in the complex forming step of forming a first complex (hereinafter also referred to as a "first complex forming step") using the first chelating agent. In the mixture, the amounts of the first complex and the second chelating agent to be added are not particularly limited. The ratio (weight ratio) between the first chelating agent used in the first complex forming step and the second chelating agent used in the second complex forming step is, for example, from 1:0.3 to 1:40, preferably from 1:7 to 1:40, more preferably from 1:10 to 1:40.

The amount of the aqueous second chelate solution to be added relative to the first complex is not particularly limited. The amount of the aqueous second chelae solution is, for example, preferably smaller than the liquid amount of the sample used. Accordingly, for example, a metal-containing liquid with a concentration higher than the sample used can be obtained. That is, a metal-containing liquid in which a metal is concentrated compared with the sample can be obtained. The amount of the aqueous second chelate solution to be added relative to the liquid amount of the sample is, for example, in the range from ½ to 1/100, preferably from 1/10 to 1/50, more preferably 1/50.

The mixture may further contain other components in addition to the first complex and the aqueous second chelate solution.

The process conditions of the second complex forming step are not particularly limited, and the process temperature is, for example, room temperature, the lower limit of the process time is, for example, 30 seconds or more, the upper limit of the process time is, for example, 60 minutes or less, preferably 30 minutes or less, and the range of the process time is, for example, from 30 seconds to 60 minutes, preferably from 30 seconds to 30 minutes.

(3b) Second Complex Recovering Step

The second complex recovering step is a step of recovering, from the mixture, a liquid fraction containing the second complex formed in the second complex forming step, dissolved therein, thereby recovering the metal.

As mentioned above, since the second chelating agent under the second insoluble pH is in a soluble state in the mixture, the second complex between the second chelating agent and the metal also is present in a soluble state in the mixture. On the other hand, the first chelating agent is present in an insoluble state in the mixture. Thus, in the second complex recovering step, the metal is recovered by recovering a liquid fraction containing the second complex dissolved therein. Although it is preferred that the second complex is completely dissolved in the mixture, the second complex may be in the state of being partially undissolved. The amount of the second complex in an insoluble state is, for example, preferably a detection limit or less.

A method for recovering the complex is not particularly limited, and a known method for separating a solid and a liquid can be employed, for example. The method for recovering the complex can be described with reference to the description of Embodiment 1, for example.

In Embodiment 3-1, the second complex recovering step may further include a chelate decomposing step of decomposing the second chelating agent in the second complex after the recovery of the liquid fraction. The metal as a single metal can be recovered from the second complex by decomposing the second chelating agent as described above. A method for decomposing the second chelating agent is not particularly limited, can be, for example, a known method such as ashing, and can be described with reference to the description of Embodiment 1.

Embodiment 3-1 is described below with reference to an example where the first insoluble pH is under acidic conditions, the second insoluble pH is under mildly acidic conditions to neutral conditions, the first chelating agent is dithizone, the second chelating agent is DMSA, the sample is an urine sample, the metal to be recovered is mercury, and the method for recovering the first complex with dithizone is filtration. This, however, is merely an example and does not limit the present invention.

A first complex is recovered in the same manner as in Embodiment 1 or 2, and the recovered first complex and an aqueous DMSA solution are mixed. Thus, a second complex is formed in the mixture of the first complex and the aqueous DMSA solution.

The aqueous DMSA solution can be prepared by dissolving DMSA in an aqueous alkaline solution, for example. The aqueous alkaline solution is, for example, preferably an aqueous trisodium phosphate solution, the concentration thereof is, for example, from 10 to 100 mmol/L, and the pH thereof is, for example, from 9 to 12. The concentration of DMSA in the aqueous DMSA solution is, for example, from 5 to 20 mg/mL. The pH of the aqueous DMSA solution is, for example, in the range from 2 to 6, preferably from 4 to 6, more preferably 4.

The amount of the aqueous DMSA solution to be added relative to the first complex is not particularly limited and is, for example, in the range from 10 to 200 µL, preferably from 20 to 100 µL, more preferably 20 µL relative to 1 mL of the urine sample. The pH of the mixture of the first complex and the aqueous DMSA solution is, for example, in the range from 2 to 6, preferably from 4 to 6, more preferably 4.

Subsequently, the mixture is subjected to solid-liquid separation, and the liquid fraction thus obtained is recovered as a second complex. A method of the solid-liquid separation is not particularly limited and can be, for example, performed with reference to the method for recovering the first complex.

Accordingly, mercury dissolved in the liquid fraction in the second complex state can be recovered. Only mercury can be recovered by decomposing the DMSA in the second complex through subjecting the second complex to wet ashing or the like, for example. Although the recovery of mercury is described above as an example, the present invention is not limited thereto.

(3-2) Embodiment 3-2

Embodiment 3-2 is, as mentioned above, an embodiment using a chelating agent represented by the following structural formula (6) as the second chelating agent and can be described with reference to the description of Embodiment 3-1 unless otherwise shown.

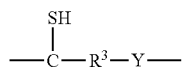
(6)

In the structural formula (6), $R^3$ represents an alkyl group or an amino alkyl group each with a carbon number of 1 or 2 or is not present, and Y represents

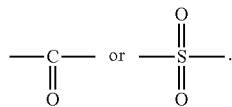

Examples of the second chelating agent include tiopronin (N-(2-mercaptopropionyl)glycine) represented by the following structural formula (6-1), DMPS (2,3-dimercapto-1-propanesulfonic acid sodium salt) represented by the following structural formula (6-2), and cysteine (2-amino-3-sulfanyl propanoic acid) represented by the following structural formula (6-3). The second chelating agent may be, for example, any of hydrates of compounds having the structural formula (6). The second chelating agent may be, for example, any of tautomers and stereoisomers thereof. Examples of the isomers include geometric isomers and conformers. As the second chelating agent, a commercially available product may be used, for example. The tiopronin is available from KANTO CHEMICAL CO., INC., Tokyo Chemical Industry Co., Ltd., Wako Pure Chemical Industries, Ltd., or the like, for example. The DMPS is available from Wako Pure Chemical Industries, Ltd. or the like, for example. The cysteine is available from NACALAI TESQUE, INC. or the like, for example. The second chelating agents may be used alone or in a combination of two or more.

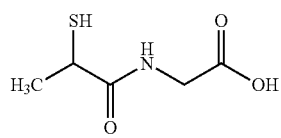
(6-1)

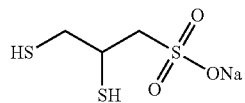
(6-2)

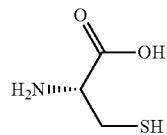
(6-3)

In the case where the second chelating agent represented by the structural formula (6) is used, the second insoluble pH can be, for example, under non-alkaline conditions, and specific examples thereof include pHs under acidic conditions (pH 1 to 3), mildly acidic conditions (pH 4 to 5), and neutral conditions (pH 6 to 7). The upper limit of the second insoluble pH is not particularly limited and is, for example, pH6.8, preferably pH6, more preferably pH4. The lower limit of the second insoluble pH is not particularly limited and is, for example, pH4, preferably pH3, more preferably pH2, yet more preferably pH 1. The second insoluble pH can be set appropriately according to the kinds and the like of the first and the second chelating agents, for example.

The concentration of the second chelating agent in the aqueous second chelate solution is not particularly limited and is, for example, from 15 to 300 mg/mL, preferably from 75 to 150 mg/mL. In Embodiment 3-2, the second chelating agent is preferably any of tiopronin, DMPS, and cysteine because they are particularly superior in solubility, for example. For example, as the concentration of the second chelating agent in the aqueous second chelate solution is increased, the amount of the formed second complex between the metal derived from the first complex and the second chelating agent is increased. Thus, the recovery yield of the metal can be further improved.

Embodiment 3-2 is described below with reference to an example where the first insoluble pH is under acidic conditions, the second insoluble pH is under mildly acidic conditions to neutral conditions, the first chelating agent is dithizone, the second chelating agent is DMPS, the sample is an urine sample, the metal to be recovered is mercury, and the method for recovering the first complex with dithizone is filtration. This, however, is merely an example and does not limit the present invention.

A first complex is recovered in the same manner as in Embodiment 3-1, and the recovered first complex and an aqueous DMPS solution are mixed. Accordingly, a second complex is formed in the mixture of the first complex and the aqueous DMPS solution.

The aqueous DMPS solution can be prepared by dissolving DMPS in a medium, for example. Examples of the medium include an aqueous trisodium phosphate solution, nitric acid, acetic acid, phosphoric acid, citric acid, a phosphate buffer solution, and a tris buffer solution. The concentration of the medium is, for example, from 10 to 100 mmol/L. The pH of the medium is not particularly limited as long as it is in the range in which dithizone is not dissolved. In the aqueous DMPS solution, the concentration of DMPS is, for example, from 5 to 20 mg/mL. The pH of the aqueous DMPS solution is, for example, in the range from 2 to 6, preferably from 4 to 6, more preferably 4.

The amount of the aqueous DMPS solution to be added relative to the first complex is not particularly limited and is, for example, in the range from 10 to 200 μL, preferably from 20 to 100 μL, more preferably 20 μL relative to 1 mL of the urine sample. The pH of the mixture of the first complex and the aqueous DMPS solution is, for example, in the range from 2 to 6, preferably from 1 to 3, more preferably 1.

Subsequently, the mixture is subjected to solid-liquid separation, and the liquid fraction thus obtained is recovered as a second complex. Accordingly, mercury dissolved in the liquid fraction can be recovered in the second complex state. Although the recovery of mercury is described above as an example, the present invention is not limited thereto. Although the present embodiment is described with reference to an example of using DMPS as the second chelating agent, a metal can be recovered in the same manner as in the present embodiment also in the case where tiopronin, cysteine, or the like is used as the second chelating agent, for example.

(4) Other Embodiments

In the metal recovery method of the present invention, the optional metal isolating step may be, for example, a method for extracting the complex with an organic solvent besides the recovery using an aqueous solvent in Embodiments 1, 2, and 3. In this case, for example, the metal isolating step may be performed according to a dithizone method (colorimetric method) or an atomic absorption method, defined in JIS K0101 or K0102.

<Method for Analyzing Metal>

As mentioned above, the method for analyzing a metal of the present invention includes: a metal recovering step of recovering a metal from a sample by the metal recovery method of the present invention; and an analyzing step of analyzing the metal. The method for analyzing a metal of the present invention is characterized in that it includes the metal recovering step of recovering a metal from a sample by the metal recovery method of the present invention, and the other steps and conditions are not particularly limited. The metal recovering step can be performed with reference to the metal recovery method of the present invention.

The analyzing step is not particularly limited and can be selected appropriately according to the kind of the metal to be analyzed, for example. The analysis of the metal can be performed by, for example, an optical measurement, GC-ECD (gas chromatography-electron capture detector), an electrochemical measurement (e.g., stripping voltammetry), or the like. The analysis by the optical measurement can be performed by measuring an absorbance, a transmittance, a reflectance, or the like using an optical analyzer or the like, for example. Examples of the optical analyzer include an atomic absorption spectrometer and a visible spectrometer. The analysis of the metal may be qualitative analysis or quantitative analysis, for example.

The method for analyzing a metal of the present invention may further include a step of correcting a measurement value, for example. In the step of correcting a measurement value, a measurement value as a measurement result can be corrected according to the correlation between the measurement value and the metal concentration in a sample, for example. The correlation can be obtained as follows, for example. A metal in the standard samples with the known metal concentrations is recovered by the metal recovery method of the present invention, and measurement values of the metal and the corresponding metal concentrations of the standard samples are plotted. It is preferred that the standard samples are in a dilution series of a metal. By correcting measurement values as described above, it becomes possible to perform the quantitative determination with higher reliability.

The metal as the above-mentioned complex may be analyzed, or the metal as a single metal obtained by isolating the metal from the complex may be analyzed, for example.

In the latter case, it is preferred that the metal recovering step includes, as mentioned above, the step of decomposing the chelating agent in the complex, i.e., the step of isolating the metal from the complex.

EXAMPLES

The examples of the present invention are described below. The present invention, however, is not limited by the following examples.

Example 1

A complex between mercury in an urine sample and a chelating agent was formed, and the mercury recovery yield in the complex formation was checked.

Example 1A

A complex was recovered in the same manner as in Embodiment 1 using an aqueous dithizone solution. Specifically, 5.56 mg of N-ethyl maleimide as a masking agent, 16.65 mg of citric acid, and 3.36 mg of sodium citrate were added to 4 mL each of five kinds of urine samples (n=5), which was then stood still for 15 minutes. 0.4 ml of 1 mmol/L citric acid-sodium citrate buffer solution (pH2) was added to the urine sample after being stood still to adjust the pH of the urine sample to be acidic pH. Subsequently, 40 μL of 0.1 mol/L aqueous sodium hydroxide solution containing 4 mmol/L dithizone (dithizone content: 0.041 mg) was added thereto to prepare a mixture. The mixture thus obtained was then shaken at 25° C. for 20 minutes using a reciprocating shaker, and a complex was formed and deposited.

The mixture was then subjected to centrifugal filtration at 300×g for 5 minutes using a column including filters arranged therein and having a diameter of 7.5 cm to separate a liquid fraction and a solid fraction. The solid fraction is a fraction containing the complex. As the filters, three kinds of glass fiber filter paper shown in Table 1 below were used, and four layers of F1, F2, F3, and F4 were arranged in the direction of an axis of the column.

TABLE 1

| Filter | Pore size |
| --- | --- |
| F1 | 23 μm |
| F2 | |
| F3 | 2.7 μm* |
| F4 | 1 μm* |

*Particle retention capacity

Then, the mercury amounts in an untreated urine sample and the liquid fraction were measured using a cold vapor atomic absorption spectrometer (MERCURY ANALYZER, produced by Nippon Instruments, Co., Ltd.). The complex recovery yield by the filters was calculated according to the following formula (1).

Complex recovery yield (%)=100×[(M−F)/M]    (1)

M: Mercury amount in mixture
F: Mercury amount in liquid fraction

Example 1B

A complex was recovered in the same manner as in Embodiment 1 using an organic dithizone solution. Specifically, the recovery yield was calculated in the same manner as in Example 1A except that 40 μL of a solution containing 4 mmol/L dithizone in acetone (dithizone content: 0.041 mg) was used as a substitute for 0.1 mol/L aqueous sodium hydroxide solution containing 4 mmol/L dithizone, and the solution was mixed with an acidic urine sample.

Example 1C

A complex was recovered in the same manner as in Embodiment 2-3 using insoluble dithizone. Specifically, in the same manner as in Example 1A, a masking agent was added to an urine sample, which was then stood still, and thereafter, 0.4 mL of 5 mmol/L aqueous sodium hydroxide solution was added to the urine sample to adjust the pH of the urine sample to be an alkaline pH. Subsequently, 0.041 mg of dithizone, 7.48 mg of citric acid, and 1.51 mg of sodium citrate were added to the urine sample, and the mixture thus obtained was then shaken for 1 minute using a reciprocating shaker to dissolve dithizone and form a complex. Further, 0.4 mL of 5 mol/L aqueous nitric acid solution was added to the mixture to neutralize the mixture. 85.54 mg of citric acid and 17.26 mg of sodium citrate were added to the neutralized mixture to adjust the pH of the mixture to an acidic pH. The acidified mixture was then shaken at 25° C. for 19 minutes using a reciprocating shaker to deposit the complex. The shaken mixture was then filtrated, and the complex recovery yield was calculated in the same manner as in Example 1A.

Comparative Example 1

In the same manner as in Example 1A, a masking agent was added to an urine sample, which was then stood still, and thereafter, 74.8 mg of citric acid, 15.1 mg of sodium citrate, and 0.041 mg of dithizone were added to the urine sample. The mixture thus obtained was then shaken at 25° C. for 20 minutes using a reciprocating shaker to form a complex. The mixture was then filtrated, and the complex recovery yield was calculated in the same manner as in Example 1.

The results of these are shown in FIG. 1. FIG. 1 is a graph showing the complex recovery yield. In FIG. 1, the horizontal axis indicates the kind of the urine sample, and the vertical axis indicates the complex recovery yield. The amount of dithizone used was the same among Examples 1A to 1C and Comparative Example 1. As shown in FIG. 1, the complex recovery yields from the urine samples of Examples 1A, 1B, and 1C were about 80% or more and only slightly varied. In contrast, the recovery yields of Comparative Example 1 were about 20% to 60% which were low and widely varied among samples. As can be seen from these results, according to the method of the present invention, a metal can be efficiently recovered through formation of the complex, and the variation in complex recovery yield among samples is removed even when the amount of the chelating agent to be used is small.

Each of the solid fractions containing the recovered complexes in Examples 1A to 1C was subjected to a concentration process using a second chelating agent. Then, a measurement of metal in the concentrated sample thus obtained was performed using a cold vapor atomic absorption spectrometer. Specifically, first, 0.4 mL of 0.1 mol/L aqueous nitric acid solution was added to the solid fraction to wash the complex, which was then subjected to centrifugal filtration to recover the complex. Subsequently, 40 μL of 0.1 mol/L aqueous nitric acid solution containing 500 mmol/L tiopronin was added to the recovered complex to elute mercury from the complex, and the mixture was then subjected to centrifugal filtration to recover a liquid fraction containing mercury. Then, the mercury amount in the liquid fraction was measured. The results of these are shown in Table 2 below.

TABLE 2

|  | Example 1A | Example 1B | Example 1C |
| --- | --- | --- | --- |
| Sample 1 | 1.51 ng | 1.14 ng | 0.65 ng |
| Sample 2 | 15.45 ng | 14.09 ng | 5.48 ng |
| Sample 3 | 1.52 ng | 1.06 ng | 0.49 ng |
| Sample 4 | 21.99 ng | 21.71 ng | 9.32 ng |
| Sample 5 | 2.12 ng | 1.99 ng | 0.79 ng |

As can be seen from Table 2, mercury can be recovered from the solid fraction containing the recovered complex in each of Examples 1A to 1C, using the second chelating agent.

Example 2

A complex between lead in an urine sample and a chelating agent was formed, and the lead recovery yield in the complex formation was checked.

Example 2A

A complex was recovered in the same manner as in Embodiment 1 using an aqueous dithizone solution. Specifically, 0.1 mol/L nitric acid was added to 10 mL of an urine sample (n=1) to adjust the pH of the urine sample to an acidic pH (pH5). Subsequently, 100 μL of 0.1 mol/L aqueous sodium hydroxide solution containing 4 mmol/L dithizone (dithizone content: 0.103 mg) was added thereto to prepare a mixture. The mixture thus obtained was then shaken at 25° C. for 20 minutes using a reciprocating shaker to form and deposit the complex.

The mixture was subjected to natural filtration using filters to separate a liquid fraction and a solid fraction. The solid fraction is a fraction containing the complex.

Then, the lead amounts in an untreated urine sample and the liquid fraction were measured using a flameless atomic absorption spectrometer (iCE3400, produced by Thermo Fisher SCIENTIFIC). The complex recovery yield by the filters was calculated according to the following formula (2). The result showed that the recovery yield was 85%. As can be seen from the result, a metal can be efficiently recovered even when the amount of the chelating agent to be used is small.

$$\text{Complex recovery yield (\%)} = 100 \times [(M-F)/M] \qquad (2)$$

M: Lead amount in mixture
F: Lead amount in liquid fraction

Example 2B

The solid fraction containing the recovered complex in Example 2A was subjected to a concentration process using each second chelating agent. Then, a measurement of lead in the concentrated sample thus obtained was performed using a flameless atomic absorption spectrometer.

100 μL of 0.1 mol/L aqueous nitric acid solution containing 500 mmol/L second chelating agent was added to the solid fraction, which was then subjected to pipetting for 1 minutes and thereafter stood still for 15 minutes to elute lead from the complex. The mixture after being stood still was then subjected to centrifugal filtration to recover a liquid fraction containing lead. Then, the lead amount in the liquid fraction was measured. As the second chelating agent, each of tiopronin, DMPS, and EDTA was used. The results of these are shown in Table 3 below.

TABLE 3

|  | Second chelating agent | | |
|---|---|---|---|
|  | Tiopronin | DMPS | EDTA |
| Lead amount | 16.12 ng | 25.41 ng | 16.03 ng |

As can be seen from Table 3, lead can be recovered from the solid fraction containing the recovered complex in Example 2A, using the second chelating agent.

Example 3

A complex between mercury in an urine sample and a chelating agent and a complex between lead in the urine sample and the chelating agent were formed, and the mercury recovery yield and the lead recovery yield in the complex formation were checked.

Example 3A

The complexes were recovered in the same manner as in Embodiment 1 using an aqueous dithizone solution. Specifically, 0.1 mol/L nitric acid was added to 10 mL of an urine sample (n=1) to adjust the pH of the urine sample to an acidic pH (pH5). Subsequently, 100 μL of 0.1 mol/L aqueous sodium hydroxide solution containing 4 mmol/L dithizone (dithizone content: 0.103 mg) was added thereto to prepare a mixture. The mixture thus obtained was then shaken at 25° C. for 20 minutes using a reciprocating shaker to form and deposit a complex.

The mixture was subjected to natural filtration using filters to separate a liquid fraction and a solid fraction. The solid fraction is a fraction containing the complexes.

Then, the mercury amounts in an untreated urine sample and the liquid fraction were measured using a cold vapor atomic absorption spectrometer. The lead amounts in the untreated urine sample and the liquid fraction were measured using a flameless atomic absorption spectrometer. The recovery yield of the complex between mercury and the chelating agent by filters and the recovery yield of the complex between lead and the chelating agent by filters were calculated according to the formulae (1) and (2). The results showed that the mercury recovery yield was 77.5%, and the lead recovery yield was 73.1%. As can be seen from the results, metals can be recovered efficiently even when the amount of the chelating agent to be used is small.

Example 3B

The solid fraction containing the recovered complexes in Example 3A was subjected to a concentration process using a second chelating agent. Then, measurements of mercury and lead in the concentrated sample thus obtained were performed using a flameless atomic absorption spectrometer.

100 μL of 0.1 mol/L aqueous nitric acid solution containing 500 mmol/L second chelating agent was added to the solid fraction, which was then subjected to pipetting for 1 minute and thereafter stood still for 15 minutes to elute mercury and lead from the complexes. The mixture after being stood still was then subjected to centrifugal filtration to recover a liquid fraction containing mercury and lead. Then, the mercury amount and the lead amount in the liquid fraction were measured in the same manner as in Example 3A. As the second chelating agent, tiopronin was used. The results of these are shown in Table 4 below.

TABLE 4

|  | Second chelating agent Tiopronin |
|---|---|
| Mercury amount | 40.5 ng |
| Lead amount | 25.0 ng |

As can be seen from Table 4, mercury and lead can be recovered from the solid fraction containing the recovered complexes in Example 3A, using the second chelating agent.

While the invention has been particularly shown and described with reference to exemplary embodiments and examples thereof, the invention is not limited to these embodiments and examples. It will be understood by those of ordinary skill in the art that various changes in form and details may be made therein without departing from the spirit and scope of the present invention as defined by the claims.

This application claims priority from Japanese Patent Application No. 2014-039593 filed on Feb. 28, 2014 and Japanese Patent Application No. 2015-036116 filed Feb. 26, 2015, the entire subject matter of which are incorporated herein by reference.

INDUSTRIAL APPLICABILITY

As described above, although the mechanism is unknown, the complex can be formed efficiently according to the present invention even when the amount of the chelating agent to be used is reduced, for example. Accordingly, a metal can be recovered with a superior yield. Thus, the present invention is really useful in clinical examinations of samples derived from biological bodies and environmental testing, for example.

The invention claimed is:

1. A method for recovering a metal, the method consisting of:
   forming, in a mixture, a complex containing a metal in a sample and a chelating agent;
   depositing the complex in the mixture; and
   recovering the deposited complex from the mixture, thereby recovering the metal in the sample,
   wherein
   the forming step and the depositing step are performed separately, wherein the forming step mixes the sample and the dissolved or partially undissolved chelating agent to bring the metal in the sample and the chelating agent in contact with each other in the mixture, thereby forming a complex, and the depositing step changes the pH of the mixture from a pH at which the chelating agent is soluble to a pH at which the chelating agent is insoluble in an aqueous solvent after the forming step, and
   wherein the complex forms when the metal reacts with the chelating agent when the chelating agent is in a dissolved state.

2. The method according to claim 1, wherein in the forming step, the sample and a chelate solution containing the chelating agent are mixed.

3. The method according to claim 2, wherein the chelate solution is obtained by dissolving the chelating agent in an aqueous solvent.

4. The method according to claim 2, wherein the chelate solution is obtained by dissolving the chelating agent in an amphipathic organic solvent.

5. The method according to claim 2, wherein the sample is a pH-unadjusted sample.

6. The method according to claim 1, wherein in the forming step, the sample and the chelating agent in an insoluble state are mixed, and the pH of the mixture is adjusted to a pH at which the chelating agent is soluble in an aqueous solvent to cause the chelating agent in an insoluble state to be in a soluble state, and bringing the metal in the sample and the dissolved or partially undissolved chelating agent in contact with each other in the mixture to form the complex when the metal reacts with the chelating agent when the chelating agent is in a dissolved state.

7. The method according to claim 6, wherein the sample is a pH-unadjusted sample.

8. The method according to claim 1, wherein in the forming step, the sample with a pH adjusted to a pH at which the chelating agent is soluble in an aqueous solvent and the chelating agent in an insoluble state are mixed to cause the chelating agent in an insoluble state to be in a soluble state, and bringing the metal in the sample and the dissolved or partially undissolved chelating agent in contact with each other in the mixture to form the complex when the metal reacts with the chelating agent when the chelating agent is in a dissolved state.

9. The method according to claim 1, wherein in the recovering step, the mixture is filtrated to recover the deposited complex.

10. The method according to claim 1, wherein the sample is urine.

11. The method according to claim 1, wherein the metal is at least one selected from the group consisting of Bi, Hg, Cd, Pd, Zn, Tl, Ag, Pb, As, and Al.

12. The method according to claim 1, wherein the chelating agent contains a sulfur-containing group.

13. The method according to claim 1, wherein the chelating agent is 1,5-diphenyl-3-thiocarbazone.

14. The method according to claim 1, wherein in the forming step, the mixture further comprises a masking agent.

15. The method according to claim 14, wherein the masking agent is at least one selected from the group consisting of maleimide, N-methyl maleimide, N-ethyl maleimide, iodoacetamide, and iodoacetic acid.

16. The method according to claim 1, wherein in the recovering step, the deposited complex is recovered, and the complex is thereafter dissolved in a solvent.

17. The method according to claim 16, wherein in the recovering step, the complex is dissolved in a solvent, and the obtained solution is concentrated.

* * * * *